US012623069B2

(12) United States Patent (10) Patent No.: US 12,623,069 B2
Budny et al. (45) Date of Patent: *May 12, 2026

(54) SELF-SUFFICIENT NEURAL TISSUE STIMULATOR

(71) Applicant: CELTRO GMBH, Dresden (DE)

(72) Inventors: Jarek Budny, Dresden (DE); Judith Piorkowski, Dresden (DE); Gerd Teepe, Dresden (DE)

(73) Assignee: CELTRO GMBH, Dresden (DE)

( * ) Notice: Subject to any disclaimer, the term of this patent is extended or adjusted under 35 U.S.C. 154(b) by 259 days.

This patent is subject to a terminal disclaimer.

(21) Appl. No.: 18/556,872

(22) PCT Filed: Apr. 29, 2022

(86) PCT No.: PCT/EP2022/061445
§ 371 (c)(1),
(2) Date: Oct. 23, 2023

(87) PCT Pub. No.: WO2022/229370
PCT Pub. Date: Nov. 3, 2022

(65) Prior Publication Data
US 2024/0198092 A1 Jun. 20, 2024

(30) Foreign Application Priority Data

Apr. 30, 2021 (EP) ..................................... 21171554

(51) Int. Cl.
*A61N 1/05* (2006.01)
*A61N 1/02* (2006.01)
(Continued)

(52) U.S. Cl.
CPC ........... *A61N 1/0551* (2013.01); *A61N 1/025* (2013.01); *A61N 1/36135* (2013.01);
(Continued)

(58) Field of Classification Search
CPC .. A61N 1/025; A61N 1/0551; A61N 1/36057; A61N 1/3606; A61N 1/36067;
(Continued)

(56) References Cited

U.S. PATENT DOCUMENTS 12,121,733 B2 * 10/2024 Teepe .................... H02J 7/0013
2014/0324113 A1 10/2014 Savage et al.
(Continued)

FOREIGN PATENT DOCUMENTS

KR 20130022419 A 3/2013
WO 2015117089 A1 8/2015
(Continued)

OTHER PUBLICATIONS

Hannan, M. et al., "Energy harvesting for the implantable biomedical devices: issues and challenges," BioMedical Engineering OnLine, vol. 13, No. 79, Jun. 20, 2014, 23 pages.
Benke, E. et al., "Architecture and Low Power Management of a Deep-tissue Medical Implant System Powered by Human Body Energy Harvesting," Proceedings of the 13th International Conference on Biomedical Electronics and Devices, Feb. 24, 2020, Valletta, Malta, 8 pages.
(Continued)

*Primary Examiner* — Amanda K Hulbert
(74) *Attorney, Agent, or Firm* — McCoy Russell LLP

(57) ABSTRACT
The invention discloses a neural tissue stimulator, characterized in that the neural tissue stimulator comprises a multiple of microneedles and a chip comprising at least one comparator with adaptive level, sequence control circuit, at least one capacitor stack built by n capacitors and 2n switches, at least one buffer capacitor outside the at least one capacitor stack, at least two additional switches outside the at least one capacitor stack, a CMOS-Logic, wherein further, the neural tissue stimulator comprises an interposer layer comprising holes for the multiple of microneedles and a lid. The neural tissue stimulator is characterized in, that the chip is located on one surface of the interposer layer and that the
(Continued)

lid and the interposer layer form a capsule for the chip. Further, the neural tissue stimulator is adapted to be electrically self-sufficient.

15 Claims, 8 Drawing Sheets

(51) Int. Cl.

| | | |
|---|---|---|
| *A61N 1/36* | (2006.01) | |
| *A61N 1/372* | (2006.01) | |
| *A61N 1/375* | (2006.01) | |
| *A61N 1/378* | (2006.01) | |

(52) U.S. Cl.
CPC ....... *A61N 1/37205* (2013.01); *A61N 1/3758* (2013.01); *A61N 1/3785* (2013.01)

(58) Field of Classification Search
CPC ............ A61N 1/36125; A61N 1/36135; A61N 1/37205; A61N 1/375; A61N 1/3756; A61N 1/3758; A61N 1/3785
See application file for complete search history.

(56) References Cited

U.S. PATENT DOCUMENTS

| | | |
|---|---|---|
| 2015/0018728 A1 | 1/2015 | Gross et al. |
| 2017/0216607 A1 | 8/2017 | Bernstein et al. |

FOREIGN PATENT DOCUMENTS

| | | |
|---|---|---|
| WO | 2018053017 A1 | 3/2018 |
| WO | 2019113451 A1 | 6/2019 |
| WO | 2021089531 A1 | 5/2021 |

OTHER PUBLICATIONS

ISA European Patent Office, International Search Report Issued in Application No. PCT/EP2022/061445, Jun. 8, 2022, WIPO, 5 pages.
ISA European Patent Office, Written Opinion of the International Searching Authority Issued in Application No. PCT/EP2022/061445, Jun. 8, 2022, WIPO, 7 pages.

* cited by examiner

SELF-SUFFICIENT NEURAL TISSUE STIMULATOR

CROSS REFERENCE TO RELATED APPLICATIONS

The present application is a U.S. National Phase of International Application No. PCT/EP2022/061445 entitled "SELF-SUFFICIENT NEURAL TISSUE STIMULATOR," and filed on Apr. 29, 2022. International Application No. PCT/EP2022/061445 claims priority to European Patent Application No. 21171554.5 filed on Apr. 30, 2021. The entire contents of each of the above-listed applications are hereby incorporated by reference for all purposes.

TECHNICAL FIELD

The invention discloses a neural tissue stimulator, characterized in that the neural tissue stimulator comprises a multiple of microneedles and a chip comprising at least one comparator with adaptive level, sequence control circuit, at least one capacitor stack built by n capacitors and 2n switches, at least one buffer capacitor outside the at least one capacitor stack, at least two additional switches outside the at least one capacitor stack, a CMOS-Logic, wherein further, the neural tissue stimulator comprises an interposer layer comprising holes for the multiple of microneedles and a lid. The neural tissue stimulator is characterized in, that the chip is located on one surface of the interposer layer and that the lid and the interposer layer form a capsule for the chip. Further, each microneedle of the array of microneedles has a distal end which protrudes from the chip, wherein the distal ends of at least two microneedles of the array of microneedles have a different electrical insoaimlation. Further, the neural tissue stimulator is adapted to be electrically self-sufficient.

BACKGROUND AND SUMMARY

Neural tissue stimulation has evolved to (i) treat chronic pain; (ii) treat neurological disorders, e.g., Parkinson's Disease and epilepsy; (iii) treat paraplegia; (iv) treat systemic diseases, e.g. arterial hypertension, sleep apnea, heart failure; and (v) connect external electronic devices to biological neural networks for data transfer and exchange.

Neural tissue stimulation (neuromodulation) has been introduced more than 30 years ago and has undergone a significant technological evolution. This was driven by (i) progress in understanding of electrical impulse propagation physiology over neural tissue such as brain, spinal cord and peripheral nerve tissue; (ii) progress in semiconductor, lead and battery technology; and (iii) progress in surgical access technologies.

Today's neural tissue stimulators typically have a diameter size of several centimeters and are placed outside the brain or the spinal cord. Long leads connect from the stimulator to the stimulation target site, where they are fixated and electrically connected to neural tissue. Limited numbers of electrodes provide connection to the stimulated target site. Leads consist of electrical wires coated with bio-compatible material. Unfortunately, over time these leads are ingrown by connective tissue.

Furthermore, until today all neural tissue stimulators are powered by a built-in chemical battery and therefore need repetitive device replacements over a patient's lifetime. This requires surgery with associated risks. Another option is to recharge the battery. These systems suffer from the fact that additional technical devices outside the patient's body must be used to charge the neural tissue stimulator, which still makes it necessary to check the neural tissue stimulator's performance status and perform a battery charging procedure either by a technician or by the patient if necessary. A procedure which is usually unfavorable for the patient.

Besides limitations in power supply, the designs of the semiconductor-to-tissue interfaces are limiting factors for clinical usage of existing neural tissue stimulation technologies.

Limited numbers of electrode numbers lack anatomical specificity of stimulated target sites with limitations to achieve desired clinical stimulation effects.

Intradural stimulation sites with extradural lead-to-battery connection require permanent lead access over the dura barrier into the intradural cavity, with the associated risks of cerebral fluid leakage and infection entrance.

Extradural electrode placement and stimulation sites exponentially decrease stimulation specificity and increase electrical energy drainage.

These factors have led to a plateau of clinical usability of current neurostimulator technologies.

Therefore, it is the purpose of the invention to overcome the above-mentioned disadvantages of the state of the art and to provide a neural tissue stimulator which is electrically self-sufficient and therefore (i) can be implanted to be fully contained in the intradural cavity, and (ii) does not need a recharge procedure for a battery or even a whole replacement by a new one due to an empty battery.

Therefore, the present invention provides a neural tissue stimulator, characterized in that the device comprises

- a multiple of microneedles forming an array of microneedles;
- a chip comprising at least one comparator with adaptive level, a sequence control circuit, at least one capacitor stack built by n capacitors and 2n switches, at least one buffer capacitor outside the at least one capacitor stack, at least two additional switches outside the at least one capacitor stack and a CMOS-Logic, wherein n∈N; wherein the n capacitors are adapted to be sequentially charged by at least one microneedle of the array of microneedles, which functions as DC input source, one after the other and wherein the 2n switches of the capacitor stack couple the n capacitors selectively to at least one microneedle of the array of microneedles and wherein the buffer capacitor outside the at least one capacitor stack is dedicated to be charged from the n capacitors of the capacitor stack at once;
- an interposer layer comprising holes for the multiple of microneedles;
- a lid;
- at least one startup circuit device;
- wherein the chip, is located on one surface of the interposer layer;
- wherein the lid and the interposer layer form a capsule for the chip;
- wherein each microneedle has a distal end which protrudes from the chip;
- wherein the neural tissue stimulator is adapted to be electrically self-sufficient due to harvesting of electrical energy from neural cells;
- wherein the distal ends of at least two microneedles of the array of microneedles have a different electrical insolation.

Further a method for stimulating neural tissue utilizing a neural tissue stimulator according to the invention is disclosed. The method is characterized in that the microneedles of the array of microneedles are inserted into neural tissue;

optionally a cellular cycle time is set;

at least one reference level for the cellular electrical activity is set;

at least one microneedle of the array of microneedles is set to emit an electrical pulse;

at least one microneedle of the array of microneedles is set to sense the amplitude of the cellular electrical activity and to harvest energy;

the amplitude of the cellular electrical activity is sensed and energy is harvested at least by one microneedle; and an electrical pulse is applied to the neural tissue by at least one microneedle of the array of microneedles;

wherein the electrical pulse is generated utilizing the harvested energy.

Device Configuration

The neural tissue stimulator according to the invention comprises a multiple of microneedles which form an array of microneedles. Every microneedle of the array of microneedles has a proximal and a distal end. In one embodiment of the invention, the microneedle according to the invention has a proximal end, which is shaped cylindrical with a diameter between 0.05 mm and 0.5 mm, preferably the proximal end has a diameter of 0.2 mm and a height between 0.05 mm and 0.5 mm, preferably with a height of 0.2 mm.

In a further embodiment of the invention the microneedle according to the invention has a proximal end which is shaped like a cuboid with a width and depth between 0.05 mm and 0.5 mm, preferably the width and depth of the cuboid is 0.2 mm. The height of the cuboid is between 0.05 mm and 0.5 mm, preferably the cuboid has a height of 0.2 mm.

From the proximal end, the microneedle comprises a tapered portion which connects a distal end with the proximal end. The distal end is needle shaped and has a length between 0.5 mm and 5.0 mm. The distal end of the microneedle is at least partially electrically conductive and shear stress resistant in the range of 5 to 50 Newton, which is comparable to the shear stress resistance of bonding wires. Preferably the microneedle is milled from one piece. Due to its length of the microneedle can be inserted into deeper layers of neural tissue, which enables targeted neural tissue stimulation. The gross anatomical structure of the entire central nervous system as well as the histoarchitecture of the human brain tissue follows a layered build-up. Therefore, neurological processes (such as certain information handling, memory function, emotions, neurohormonal regulation, motor actions and others) are localized in distinct anatomical target zones in distinctly different depth layers of the central nervous system. Medical neurostimulation requires precise localization and depth of stimulus deployment to reach the desired target zone driven by the clinical use case scenario. For that existing electrode designs are limited. The present invention enables unique new features for highly specific brain tissue stimulation especially with respect to the reach into deeper layers of neural tissue.

Preferably, the diameters of the distal ends of the multiple of microneedles are between 0,001 mm and 0.1 mm, preferably between 0.01 mm and 0.1 mm, most preferably the diameters of the distal ends of the multiple of microneedles are 0.02 mm. Thereby, the distal ends of the microneedles approximate neural cellular dimensions. The dimensions of the microneedles are therefore a lot smaller than any other electrodes in use today. In one embodiment of the invention up to approximately 5 microneedles can be positioned per $mm^2$ on a chip.

The small dimensions of the microneedles offer several advantages over the state of the art. Firstly, microneedles according to the invention couple directly electrically to only a few distinct nerve cells or their axons. This allows highly selective targeting of stimulation to areas in the brain/spinal cord, which are exclusively needed (e.g. movement-dependent stimulation of motoneuron axons in patients after spinal cord injury). Unintended and potentially painful stimulation to neighboring neural structures can be avoided. Further, the high number and redundancy of microneedles within the array allow for individualized programming of neural tissue stimulation depending on anatomy and structure of the neural target tissue in any given patient. Further, microneedles according to the invention are able to sense cellular electrical activity, harvest energy directly from inside the neural tissue and/or emit an electrical pulse directly into the neural tissue due to their small dimensions. Thereby, advantageously the stimulation threshold is lowered.

Further due to the fact that the neural tissue stimulator according to the invention is able to harvest energy no external energy supply e.g. by a battery is necessary. Advantageously, this allows that the entire device can be implanted to be fully contained within the intradural cavity for brain and spinal cord applications. This will avoid medical implants which permanently cross the dura barrier with the risk of cerebral liquor leakage and intracerebral infection routes. State of the art devices are not suitable for this purpose, since conventional electrodes connect from within the brain tissue to externally implanted battery/electronics.

In one preferred embodiment of the invention the neural tissue stimulator is adapted to be implanted in living beings in a way to be fully contained within the intradural cavity. This is enabled since no external energy supply is necessary and further the dimensions of the neural tissue stimulator can be adapted to the dimensions of the implantation site in the body. The device of the invention is suited to be inserted and used in living beings, which means in human being as well as in animals.

In one embodiment of the invention all microneedles of the array of microneedles have the same length. In a further embodiment of the invention the microneedles of the array of microneedles have different lengths. Advantageously, in the latter embodiment the microneedles of the array of microneedles can be adapted in length to reach certain depth layers of neural tissue with different functionality and information content.

In a preferred embodiment of the invention the neural tissue stimulator comprises between 5 and 1 000 000 microneedles, preferably between 25 and 10 000 microneedles, most preferably between 100 and 2500 microneedles.

Principally the multiple of microneedles can be arranged on the chip in every way. In a preferred embodiment of the invention, the multiple of microneedles is arranged symmetrically to each other on the chip. Thereby, advantageously a largest possible number of microneedles can be arranged on the surface of the chip. Further, the regularity in the order of the microneedles simplifies production processes.

The microneedles comprise a material of the group comprising Platin/Iridium (PtIr), gold, and fine metals. The material of the microneedles should be suitable for solder-connection with the chip or the interposer layer. Further, according to the invention, all materials comprised in the multiple of microneedles are bio-compatible and insensitive to body liquids. Bio-compatible in conjunction with the present invention means that no toxic interactions occur between the bio-compatible material and tissue, e.g. human tissue.

Further, preferably, each microneedle is adapted to be able to harvest cellular energy, to electrically stimulate live tissue and to sense intrinsic cellular electrical activity. According to the invention, every microneedle of the multiple of microneedles is operable independent of the other microneedles. Which means that one microneedle could harvest energy while a neighboring microneedle is sensing intrinsic cellular electrical activity. The tasks of each microneedles can be redistributed at any time and thus adapted to the current requirements of the neural tissue stimulator.

According to the invention at least two microneedles of the array of microneedles have different electrical insolation. Which means that the distal end of at least one microneedle is partially covered by an electrically insulating material, thereby not the whole distal end of this microneedle is electrically conductive. By covering the distal ends of different microneedles of the array of microneedles at different length with an electrically insulating material it is possible to stimulate different depth layers of the central nervous system. This feature is enormously beneficial to enable a local high resolution stimulation. A good example for the associated advantages is spinal cord stimulation for paraplegia. The problem with conventional electrodes is that the stimulation of larger areas/depths is too imprecise, resulting in painful side effects and unwanted movements. This does not occur using the device of the present invention.

Suitable electrically insulating material for covering the distal end of a microneedle can be selected from the group comprising Parylene-C and other plastics, Silicon Dioxide ($SiO_2$) and other ceramics. These materials are bio-compatible and insensitive to body liquids.

In one embodiment of the in invention the distal end of one microneedle is partially covered by an electrically insulating material and all other microneedles of the array of microneedles are uncovered. In a further embodiment the distal end of more than one microneedle of the array of microneedles is covered by an electrically insulating material, wherein the distal ends of at least two microneedles are covered by an electrically insulating material at a different length.

Further, the neural tissue stimulator according to the invention comprises a chip and an interposer layer. In one embodiment of the invention the proximal end of each microneedle is soldered to the surface of the chip, which ensures that each microneedle of the array of a multiple of microneedles has a direct contact to the chip. In a further embodiment of the invention the proximal end of each microneedle is soldered to the surface of the interposer layer of the neural tissue stimulator. According to the invention each microneedle of the array of a multiple of microneedles is isolated from each other microneedle of the array of a multiple of microneedles. Further, the distal end of every microneedle protrudes from the chip and/or the interposer layer.

According to the invention the chip comprises all devices necessary to control the neural tissue stimulator's functions. Therefore, the chip comprises at least one comparator with adaptive level, a sequence control circuit, at least one capacitor stack built by n capacitors and 2n switches, at least one buffer capacitor outside the at least one capacitor stack, at least two additional switches outside the at least one capacitor stack and a CMOS-Logic, wherein n E N.

Self-Sufficiency Energy Harvesting

In a preferred embodiment of the invention the chip comprises at least one comparator with adaptive level, at least one capacitor stack built by n capacitors and 2n switches, at least one buffer capacitor outside the at least one capacitor stack, at least two additional switches outside the at least one capacitor stack for each needle of the array of microneedles.

According to the invention the 2n switches of the at least one capacitor stack couple the n capacitors selectively to at least one microneedle of the array of microneedles. Further, the n capacitors of the at least one capacitor stack are dedicated to be sequentially charged by at least one microneedle of the array of microneedles one after the other. And the at least one buffer capacitor outside the at least one capacitor stack is dedicated to be charged from the n capacitors of the capacitor stack at once.

Hence, the chip according to the invention comprises at least one capacitor stack, wherein the capacitor stack is built by n capacitors and 2n switches, wherein n∈N. The capacitor stack can comprise as much capacitors as can be accommodated constructively. In one embodiment of the invention n is between 2 and 20, more preferably between 2 and 14. The n capacitors of the capacitors stack are dedicated to be sequentially charged by at least one microneedle of the array of microneedles, which functions as DC input source, one after the other.

The 2n switches of the capacitor stack couple the n capacitors selectively to at least one microneedle of the array of microneedles in a way that every capacitor is sequentially charged by the DC input made available by the at least one microneedle of the array of microneedles one after the other. The DC input is made available since the microneedles couple directly electrically to neural cells and derive the electrical signal. Thereby, the DC input by the neural cells can be intermittent, which means the DC-voltage is not always present. The controlling and sequencing of the switches is generated from a usual CMOS-Logic, which is common to Microelectronics.

At least one buffer capacitor is situated outside the capacitor stack, which works as a buffer. According to the invention, the at least one buffer capacitor is dedicated to be charged from the n capacitors of the at least one capacitor stack at once. In a preferred embodiment of the invention, the chip comprises one buffer capacitor outside the capacitor stack. In a further preferred embodiment of the invention the chip comprises two buffer capacitors outside the capacitor stack.

Furthermore, the chip comprises at least two additional switches outside the capacitor stack. In a preferred embodiment of the invention the chip comprises two additional switches outside the capacitor stack. The additional switches are dedicated to selectively couple the capacitor stack to the at least one buffer capacitor outside the capacitor stack or to a further optional capacitor stack.

In a further preferred embodiment the chip comprises four additional switches outside the capacitor stack. Preferably the chip comprises four additional switches outside the at least one capacitor stack if the chip comprises a first buffer capacitor outside the at least one capacitor stack and a second buffer capacitor outside the at least one capacitor stack. In this embodiment two additional switches are dedicated to selectively connect the at least one capacitor stack to the first buffer capacitor outside the capacitor stack and the two further additional switches are dedicated to selectively connect the at least one capacitor stack to the second buffer capacitor outside the capacitor stack.

Accordingly, in one preferred embodiment the chip according to the invention comprises two buffer capacitors outside the capacitor stack as buffer capacitors outside the at least one capacitor stack and four additional switch outside the at least one capacitor stack.

From its physical construction as a stack, the n capacitors of the capacitor stack are all connected in series electrically. Furthermore, in one embodiment of the invention, the at least one capacitor stack comprises at least three conductive plates wherein the conductive plates have a top-side and a bottom-side and wherein the top-side of at least one conductive plate is part of a first capacitor and the bottom-side of the at least one conductive plate is part of a neighboring further capacitor. Furthermore, the capacitor stack comprises an isolating material between the conductive plates in a way that a capacitor is built.

In a preferred embodiment of the invention, a capacitor stack with n capacitors comprises m=n+1 conductive plates. According to the invention the first conductor n=1 is built between the bottom-side of the first conductive plate (m=1) and the top-side of the second conductive plate (m=2). The neighboring conductor (n=2) is built between the bottom-side of the second conductive plate (m=2) and the top-side of the third conductive plate (m=3) and so on.

The capacitance of the capacitors built according to the invention is quite wide ranging from 1 nF down to 1 fF and even below. It depends on plate geometries and the dielectric material employed between the plates. Typical dielectric materials are SiO2 or plastic, but other dielectric materials are possible.

The arrangement of the conductors in a capacitor stack with n capacitors according to the invention has the advantage that the inner conductive plates, which means plates m=2 to m=n form no or just very small parasitic capacitances to the outside of the stack. Parasitic capacitances are well known in the art. They arise at the interfaces of capacitors to the surrounding and are unwanted as those have to be charged at every charge cycle of the capacitor. This process lowers the charging efficiency of the capacitor and therefore its end-charging voltage. Accordingly, in the state of the art every capacitor has two interfaces to the surrounding and therefore two interfaces where parasitic capacitances arise.

The capacitor stack according to the invention is able to provide n capacitors, wherein only the first and the last capacitor have a substantial interface to the surrounding. Therefore, advantageously, only at these two interfaces parasitic capacitances will form. Accordingly, the charging efficiency of the n capacitors of the capacitor stack is increased as well as the end-charging voltage.

Furthermore, in a preferred embodiment of the invention, all capacitors are connected in series electrically.

In one preferred embodiment of the invention the at least one capacitor stack built by n capacitors and 2n switches, the at least one buffer capacitor outside the at least one capacitor stack and the at least two additional switches outside the at least one capacitor stack are configured as an integrated circuit wherein switches are realized as transistors and capacitors are realized by conductive plates from integrated circuit technology.

Preferably the conductive plates are made of material selected from the group comprising metal or polysilicon or any other conductive material from integrated circuit technology. Suitable metals are copper and aluminum and tungsten.

In one embodiment of the invention the isolating material is selected from the group comprising $SiO_2$, SiN and $Hf_2O$ and stacks thereof.

As described above the capacitor stack is internally nearly perfect if it comes to storing the applied charges, as the field is nicely confined internally. Unfortunately at the first and last conductive plates still some parasitic capacitances will form. In view not to lose the energy stored in those external parasitic capacitances, according to the invention, an inductor can be applied to perform intermediate storage in a resonant circuit configuration.

Accordingly, in one embodiment of the invention the chip comprises additionally an inductor. Preferably small inductors are integrated monolithically in the integrated circuit. According to the invention the switching frequency is chosen high enough so that the resonant frequency of the parasitic capacitor and the inductivity equals the inverse of the total charging/discharging cycle time of the capacitor stack. In addition the charging/discharging timing of the capacitor stack should be adapted such that a sine-curve is approximated.

Practical inductivity values in integrated circuits will be in the range 1-10 µH when 100 windings will wrap around a typical chip of 25 mm² size. Parasitic capacitor values will range between 1-10 pF for a typical capacitor stack. For this setting, the resonance frequencies will be found between 10-200 MHz. The charging frequencies of the capacitances in the capacitor stack in consequence will have to be 2n higher.

In another preferred embodiment the chip comprises several capacitor stacks wherein every capacitor stack is dedicated to charge another capacitor stack and one capacitor stack is dedicated to charge at least one buffer capacitor outsides the capacitor stacks. Thereby, cascading of the sequential small charge collection according to the invention is possible.

Several capacitor stacks are preferably connected by switches outside the capacitor stacks, most preferably always two capacitor stacks are connected by two switches outside the capacitor stacks. In one embodiment of the invention the device comprises x capacitor stacks and 2x switches outside the capacitor stacks, wherein x∈N. In one embodiment of the invention the device comprises 1 to 20 capacitor stacks, preferably 5 to 15, most preferably 13 to 15, as this is within the capabilities of current semiconductor production technologies.

However, the charging frequency of a further capacitor stack is n-times slower than the charging frequency of the first capacitor stack (with n being the number of capacitors in the first capacitor stack). In principle the n capacitors of the first capacitor stack are charged by the DC input of at least one microneedle of the array of microneedles one after the other. Afterwards the n capacitors of the first capacitor stack are discharged at once to one capacitor of a further capacitor stack. In case the further capacitor stack is built by k capacitors, k charging cycles are needed to charge the k capacitors of the further capacitor stack one after the other, wherein k∈N. If all capacitors of the further capacitor stack are charged they are discharged to a further capacitor outside the capacitor stack at once. In total, the entire discharge occurs at a frequency k·n lower than the charging frequency of the first capacitor stack. The maximum voltage of the second stack is k·n the feeding voltage of the DC input source. For example with 10 mV at the at least one microneedle of the array of microneedles, and 10 capacitors on each capacitors stack, 1 V can be realized as output at maximum.

According to the invention, every further capacitor stack is dedicated to be fed by positive or negative voltages from another capacitor stack. Therefore, the switches outside the capacitor stacks connecting the capacitor stacks have to be sequenced accordingly. If the first capacitor stack provides positive or negative charge, charging of the second capacitor stack has to be done accordingly.

In an embodiment of the invention the sequencing of the switches is generated from a usual CMOS-Logic, which is common to Microelectronics. For the CMOS-logic to function, voltages of a few hundred millivolts are required. Typical state of the art semiconductor technology operates at around 1 Volt or slightly below. Since the neural tissue stimulator according to the invention collects energy starting with a few millivolts at the source, this voltage is too low to operate the CMOS-logic.

Startup Circuit

However, after collection and cascading, voltages in the 1-Volt domain can be obtained, which is enough to operate the CMOS-logic. For this reason, a startup circuit is required, to make sure the logic can be powered and the switches are operated to perform energy collection from the tiny sources.

According to the invention the device comprises at least one startup circuit device to provide the CMOS-logic with startup energy. Therefore, in one embodiment the startup circuit device is selected from a group comprising at least one coil, at least one antenna, a Peltier element and/or a Piezo element. Accordingly, in one embodiment of the invention the CMOS-logic is powered with startup energy by a magnetic coupling over coils or by at least one antenna.

In one embodiment the device comprises at least one coil. For this, a magnetic coupling over coils is proposed. The outer coil is excited with alternate current, creating a magnetic alternating field. Through this field the startup energy is transmitted to the coil on the integrated circuit, which recuperates the startup energy.

In one embodiment of the invention the invention the neural tissue stimulator comprises at least one coil. Preferably the coil is dedicated to receive a startup energy by magnetic coupling with another coil. In one embodiment the at least one coil is located on the interposer layer. In a further embodiment of the invention the at least one coil is part of the chip in the sense that the at least one coil is wound around the chip. However, in each of these embodiments the chip comprises an interface for power management to connect the at least one coil of the neural tissue stimulator to the CMOS-logic comprised on the chip.

In one embodiment of the invention the neural tissue stimulator comprises at least one further capacitor. The at least one further capacitor can be located on the interposer layer outside the chip or which is comprised on the chip, wherein the latter is preferred. The at least one further capacitor of the neural tissue stimulator serves preferably as buffer capacitor for all microneedles of the array of microneedles and the capacitor stacks assigned to them. Furthermore, the at least one further capacitor of the neural tissue stimulator can serve for energy transfer from an external energy source, e.g. for the startup process. In one embodiment the at least one further capacitor is connected to the chip by the interface for power management comprised on the chip.

In a further embodiment the device comprises at least one antenna. In one embodiment the at least one antenna is positioned on the interposer layer. In a further embodiment the device comprises two antennas, which are preferably positioned on the interposer layer. In these embodiments the chip comprises an interface for power management to connect the at least one antenna of the device to the CMOS-logic comprised on the chip. The at least one antenna transforms radio waves propagating through space into electrical current moving in a conductor, namely the antenna. In this case the antenna works as a receiver antenna. Thereby, the startup energy is transmitted to the CMOS-logic. Further, the at least one antenna can work as a transmitter to transmit data in and out of the device. The antenna can be for example a dipole antenna like a throw antenna. In one embodiment of the invention the at least one antenna has a length between 1 cm and 5 cm.

In a further embodiment the device comprises at least one coil and at least one antenna.

Programmability

Further, the chip of the neural tissue stimulator according to the invention is adapted to communicate with an external programmer unit. External means that the unit must not be in direct contact with the patient at all. The communication is preferably done via externally applied electromagnetic fields. Accordingly, in one embodiment the neural tissue stimulator further comprises at least one coil to communicate with the external programmer unit, thereby the coil functions as receiver and transmitter. Furthermore, the chip comprises an I/O interface for data transmission from the external programmer unit via the coil of the neural tissue stimulator to the chip. This has the advantage, that the functionality of the neural tissue stimulator can be proofed, surveyed and adjusted from the external programmer unit. Hence, adjustments in the functionality of the neural tissue stimulator are possible through the tissue and without physical contact to the neural tissue stimulator. Accordingly in a preferred embodiment of the invention the neural tissue stimulator further comprises an external programmer unit. The external programmer unit is selected from a group comprising tablets, smartphones and PC's. The external programmer unit is adapted to communicate with the neural tissue stimulator, therefore in a preferred embodiment a coil for transmitting and receiving is comprised in the external programmer unit.

Accordingly in one embodiment of the invention the neural tissue stimulator comprises at least two coils, wherein one coil is adapted to receive a startup energy for the CMOS-logic and one coil is adapted to function as receiver and transmitter to the external programmer unit. Both coils can be located on the interposer layer or can wound around the chip as already described. In another embodiment one coil can be located on the interposer layer and another coil can be wound around the chip.

Advantageously, in a preferred embodiment the coil which is comprised in the neural tissue stimulator and uses to communicate with the external programmer unit and the coil which is comprised in the neural tissue stimulator and used to receive a startup energy for the CMOS-Logic are the same coil.

Interposer Layer

Further the neural tissue stimulator according to the invention comprises an interposer layer and a lid.

The interposer layer serves as assembly platform for the chip and is mechanically flexible in a way, that the neural tissue stimulator can be adapted to the spinal cord surface of a living being.

The interposer layer comprises a material of the group comprising FR4 materials, epoxy-resin, Poly(methyl methacrylate) (PMMA), ceramics, silicon, silicon dioxide (SiO$_2$), glass and plastics. FR4 materials are a class of flame-resistant composite materials comprising woven fiberglass and epoxy resin. Principally, the materials comprised in the interposer layer have to be non-electrically conductive. Further, according to the invention all materials comprised in the interposer layer are bio-compatible and insensitive to body liquids.

In one embodiment of the invention the interposer layer comprises holes, each hole being suitable for the distal end of a microneedle to pass through. According to the invention the interposer layer comprises a hole for each microneedle of the array of microneedles. Thus, in a preferred embodiment the interposer layer comprises as many holes as the array of a multiple of microneedles comprises microneedles. In this embodiment the microneedles are soldered to a surface of the chip.

The chip is positioned on top of the interposer layer and the microneedles of the array of a multiple of microneedles pass through the holes in the interposer layer. Hence, every microneedle of the array of microneedles passes through a separate hole in the interposer layer. Advantageously, the holes in the interposer layer are arranged in a way that all microneedles of the array of a multiple of microneedles which are soldered to the chip can pass through without making contact to the interposer layer.

Every hole in the interposer layer with a microneedle passing through is sealed to the surrounding with a non-conductive material. Suitable non-conductive materials are for example epoxy-resin, Poly(methyl methacrylate) (PMMA), glass and plastics. Thereby, no fluids from the environment can penetrate to the chip through the holes.

In a further embodiment each microneedle of the array of microneedles is soldered to the interposer layer. In this embodiment the interposer layer comprises a wiring connecting each microneedle of the array of microneedles to the chip, thereby connecting each microneedle of the array of microneedles to at least one capacitor stack.

In one embodiment the neural tissue stimulator further comprises at least one further capacitor and/or at least one sensor. In this embodiment the interposer layer comprises a wiring connecting the chip, the at least one senor and the at least one further capacitor with each other.

Further, in one embodiment the interposer layer serves as assembly platform for the at least one further capacitor and/or the at least one sensor and/or the at least one coil of the neural tissue stimulator. In this embodiment the at least one further capacitor and/or the at least one sensor and/or the at least one coil are preferably positioned next to the chip on the interposer layer.

According to the invention the neural tissue stimulator further comprises a lid. The lid covers the chip from the surrounding, wherein the lid is sealed to the interposer layer. Sealing can be done by adhesives or soldering tin. If adhesives are used the adhesive should be hardened. However, the sealing should be bio-compatible and insensitive to body fluids. Accordingly, the lid and the interposer layer form a capsule for the chip. The lid and the interposer layer shield the electronic parts from surrounding body-fluids like blood, e.g. from body fluids by forming a capsule.

In one embodiment of the invention next to the chip on top of the interposer layer at least one capacitor and/or at least one coil are positioned. The chip, the at least one capacitor and/or the at least one coil are located on one surface of the interposer layer and the lid covers the chip, the at least one capacitor and/or the at least one coil from the surrounding, wherein the lid is sealed to the interposer layer, as already described. Thereby, the lid and the interposer layer form a capsule for the chip, the at least one capacitor and/or the at least one coil. Preferably, the lid and the interposer layer shield all electronic parts comprised in the neural tissue stimulator from surrounding body-fluids like blood, e.g. from body fluids by forming a capsule.

The lid comprises a material of the group comprising FR4 materials, epoxy-resin, Poly(methyl methacrylate) (PMMA), ceramics, silicon, silicon dioxide ($SiO_2$), glass and plastics and metals. Suitable metals are for example aluminum, or aluminum vaporised with tungsten. According to the invention all materials comprised in the lid are bio-compatible and insensitive to body liquids.

Fixation between the neural tissue stimulator and the neural tissue is obtained through biological adhesives (e.g, fibrin-based materials) attached to capsule and interposer layer.

The neural tissue stimulator according to the invention can have various shapes. Preferably the neural tissue stimulator has an I-shape, T-shape, H-shape, circular or O-shape. Due to the shaping the neural tissue stimulator of the invention can be easily adapted to be placed in various anatomical target locations: (i) on the surface or within the brain, (ii) on the surface or within the spinal cord, (iii) on the surface or wrapped around peripheral nerve structures.

In one embodiment the neural tissue stimulator has an I-shape with a length between 1 mm and 8 cm, preferably between 1 cm and 5 cm, most preferably between 1.5 cm and 3 cm. The width of the I-shape neural tissue stimulator is between 1 mm and 3 cm, preferably between 5 mm and 2 cm, most preferably between 5 mm and 1 cm.

In a further embodiment the neural tissue stimulator has a T-shape with a main body and one wing on each side of the main body. The length of the main body is between 1 mm and 8 cm, preferably between 1 cm and 5 cm, most preferably between 1.5 cm and 3 cm. The width of the main body is between 1 mm and 3 cm, preferably between 5 mm and 2 cm, most preferably between 5 mm and 1 cm. Both wings of the T-shaped neural tissue stimulator are positioned mirror-symmetrically to the main axis of the main body and have the same dimensions. The length from the end of the first wing across the main body to the end of the second wing is between 1 mm and 3 cm, preferably between 5 mm and 2 cm, most preferably between 1 cm and 2 cm. The width of a wing on the widest point is between 1 mm and 3 cm, preferably between 5 mm and 2 cm, most preferably between 5 mm and 1 cm.

In a further embodiment the neural tissue stimulator has an H-shape with a main body and two wings on each side of the main body. The length of the main body is between 1 mm and 8 cm, preferably between 1 cm and 5 cm, most preferably between 1.5 cm and 3 cm. The width of the main body is between 1 mm and 3 cm, preferably between 5 mm and 2 cm, most preferably between 5 mm and 1 cm. All 4 wings of the H-shaped neural tissue stimulator are positioned mirror-symmetrically to the main axis of the main body, with 2 wings on each side of the main body. All wings and have the same dimensions. The wing-pair length from the end of the first wing across the main body to the end of the second wing is between 1 mm and 3 cm, preferably between 5 mm and 2 cm, most preferably between 1 cm and 2 cm. The width of a wing on the widest point is between 1 mm and 3 cm, preferably between 5 mm and 2 cm, most preferably between 5 mm and 1 cm. The longitudinal distance between the 2 wing-pairs is between 1 mm and 7 cm, preferably between 5 mm and 3 cm, most preferably between 5 mm and 2 cm.

The edges of the T-shaped or the H-shaped neural tissue stimulator can be rounded.

In a further embodiment the neural tissue stimulator has a circular or an O-shape. The circular shape has a diameter between 1 mm and 8 cm, preferably between 5 mm and 4 cm, most preferably between 5 mm and 2 cm. The oval O-shape has a length between 1 mm and 8 cm, preferably between 1 cm and 5 cm, most preferably between 1.5 cm and 3 cm and a width between 1 mm and 3 cm, preferably between 5 mm and 2 cm, most preferably between 5 mm and 1 cm The neural tissue stimulator is between 3 mm and 10 mm, preferably between 3 mm and 8 mm, most preferably between 3 mm and 5 mm high.

Thereby, the neural tissue stimulator according to the invention is smaller than any currently available neural tissue stimulator. This offers several advantages, first of all a neural tissue stimulator of this size can be implanted directly into the intradural cavity. Due to its small dimensions the neural tissue stimulator according to the invention grows better into the tissue, is less susceptible to infections and is less prone to dislocation.

Since the neural tissue stimulator according to the invention is adapted to sense cellular electrical activity and to generate an electrical pulse if necessary, the neural tissue stimulator according to the invention provides all functions that are required by a neural tissue stimulator. Advantageously, the neural tissue stimulator according to the invention is adapted to be electrically self-sufficient.

According to the invention, the chip comprises a sequence control circuit. This circuit controls the functionality of the neural tissue stimulator and determines the workflow of the functions of the neural tissue stimulator. All interfaces comprised on the chip like I/O-interface and interface for power management are interfaces to the sequence control circuit.

Sensing

Sensing of cellular electrical activity requires measurement of the amplitude of the actual potential with regards to a reference level or ground. Generally, this is performed with a comparator circuit. For the neural tissue stimulator according to the invention sensing is important for energy harvesting and in some case also for timing a stimulation process. The measurement of the nerve cell potential is standard and in use with current neural tissue stimulators.

According to the invention, the chip comprises at least one comparator with adaptive reference level. In a preferred embodiment of the invention the chip comprises a comparator with adaptive reference level for each microneedle of the array of microneedles, wherein each microneedle of the array of microneedles is electrically connected to one comparator circuit on the chip.

According to the invention, every microneedle of the array of microneedles is adapted to be able to sense the amplitude of the intrinsic cellular electrical activity by the standard procedure of measurement of nerve cell potential. Advantageously, these measurements can be performed on one microneedle of the array of microneedles, on selected microneedles of the array of microneedles or on all of the microneedles of the array of microneedles. The redundancy of microneedles in the array of microneedles provides a number of beneficial features. How many and which of the microneedles of the array of microneedles perform sensing is programmed via the external programmer unit.

In one embodiment the cellular electrical activity is sensed continuously. In a further embodiment of the invention the cellular electrical activity is sensed in a way that it is monitored when the amplitude of the cellular electrical activity exceeds a reference level, when the amplitude of the cellular electrical activity falls below the reference level and what the maximum amplitude of the cellular electrical activity during a cellular cycle is. Thereby, timing points of the individual progression of the nerve cell activation are monitored. Further, the amplitude of the cellular electrical activity is sensed by at least one microneedle of the array of microneedles and recorded by the external programmer unit or in one embodiment by an internal data memory device, which is comprised in the neural tissue stimulator. In case the amplitude of the cellular electrical activity is recorded by an internal data memory device, the chip according to the invention further comprises a suited internal memory device.

Further, the amplitude of the actual nerve cell potential sensed by the microneedles of the array of microneedles selected for sensing of cellular electrical activity is compared to a reference level by the at least one comparator. In one embodiment of the invention the at least one comparator comprises more than one reference level. This could be implemented by a multi bit A/D converter. Principally the reference level for each comparator is programmable. In one embodiment of the invention a reference level is programmed individually for each microneedle of the array of microneedles. In a further embodiment of the invention, the reference level is the same for each comparator comprised on the chip. In one embodiment of the invention the reference level of the at least one comparator is programmable between 0.1 mV and 10.0 mV.

Hence, the reference level can be the same for all microneedles of the array of microneedles sensing the cellular electrical activity but can also be different for each microneedle of the array of microneedles. By programming the reference level of each comparator individually, optimized timing points for all microneedles of the array of microneedles which are penetrating the tissue at different positions can be provided. This is very advantageously, since the timing of all functions of the neural tissue stimulator according to the invention can be programmed according to individual progression of the nerve cell activation. This increases safety and accuracy aspects, since the cellular electrical activity is sensed by several individual microneedles of the array of microneedles, which can be understood as sensing with several tiny individual electrodes with a high spatial resolution. Further if one microneedle of the array of microneedles does not function correctly another microneedle can be programmed to perform sensing function. Accordingly, sensing function is provided in a redundantly way. In contrast, in state-of-the-art neural tissue stimulators only few electrodes are provided for sensing cellular electrical activity. This is imprecise in terms of spatial resolution and if these electrodes do not function correctly, the neural tissue stimulator has to be replaced. Hence, the neural tissue stimulator according to the invention improves functionality and reduces the risk of new operations.

Further, the efficiency of the neural tissue stimulator is increased compared to state of the art neural tissue stimulators, since the microneedles of the array of microneedles used for performing energy harvesting and/or sensing of cellular electrical energy and/or for emitting an electrical pulse can be selected depending on pre-specified position and function of the respective microneedles of the array of microneedles. Accordingly, the microneedles of the array of microneedles are freely programmable after implant into the body and are reconfigurable via the external interface.

Harvesting

According to the invention, every microneedle of the array of microneedles is adapted to harvest cellular energy. The brain is a big organ and transforms chemical energy (sugar) into electrical energy (nerve cell activation). This process is controlled and conducted through the spread of electrical energy over all nerve cells. Each cell acts as a battery which is discharged and charged once during each cellular cycle. That function is mediated by the exchange of Sodium and Potassium through ion channels in the cellular membrane. The actual electrical energy turnover of an individual cell is small, however, harvesting from multiple cells and multiple times can collect a significant amount of electrical energy.

Even if the transmembrane voltages cannot be directly accessed, as the microneedles of the array of microneedles are too large to reach an individual intracellular space, portions of the produced cellular electrical energy are collectible from the outside intercellular space. As one microneedle of the array of microneedles touches a sequence of cells (approximately 100 cells or more) which operate synchronously, the collectable energy increases. Accordingly, the DC-input source can be intermittent, which means the DC-voltage is not always present.

Harvesting is done by a method comprising at least one capacitor stack build by n capacitors and 2n switches, at least one buffer capacitor outside the capacitor stack, at least two additional switches and at least one microneedle of the array of microneedles as DC input source, comprising the steps the n capacitors of the capacitor stack are sequentially charged by coupling one capacitor after the other to at least one microneedle of the array of microneedles by selectively closing the switches;

discharging the n capacitors of the capacitor stack into the at least one buffer capacitor outside the capacitor stack;

wherein the at least one microneedle of the array of microneedles couples directly electrically to nerve cells, thereby functioning as DC input source. Steps a. and b. define one harvesting cycle. According to the invention the DC-input source can be intermittent, which means the DC-voltage is not always present.

In a preferred embodiment of the method of the invention the n capacitors of the capacitor stack are sequentially charged one after the other in n charging cycles and the n capacitors of the capacitor stack are discharged in an $n+1^{st}$ cycle into at least one buffer capacitor outside the capacitor stack at once.

Fundamentally, the capacitors of a capacitor stack could be charged in any order. However, in order to reduce the recharging of the parasitic capacitances which arise at the interfaces to the surrounding, the following charging scheme is proposed. According to a preferred embodiment of the invention, the n capacitors of the capacitor stack are sequentially charged one after the other in n charging cycles, wherein the first capacitor is charged, afterwards the capacitor which is next to the first one is charged, afterwards the capacitor which is next to the one charged before is charged until all n capacitors are charged.

If all capacitors of a capacitor stack are charged, the capacitors of the capacitor stack are all discharged into at least one buffer capacitor outside the capacitor stack at once. This is done by selectively closing the switches of the capacitor stack and the switches outside the capacitor stack.

In a further embodiment of the invention a bipolar charging of the capacitor stack can be done. Fundamentally, each capacitor of a capacitor stack can be charged to positive or negative voltages, depending which plate of the capacitor is grounded. As already described, capacitors in the capacitor stack are being loaded sequentially. While one plate is grounded, the other plate is charged to a fraction of the input voltage. Which means, that capacitors in the capacitor stack above the currently grounded plate are pushed to positive voltages, whereas the plates below the currently grounded plate are pushed to negative voltages. Accordingly, the capacitors of the capacitor stack can be charged to positive or negative voltages, by closing the switches inside the capacitor stack in an appropriate manner, thereby selecting the grounded plate of the each capacitor in the capacitor stack.

If bipolar charging of the capacitor stack is done, preferably two buffer capacitors outside the capacitors stack are used as buffer capacitors. In this embodiment of the invention the at least one capacitor stack is first charged with positive voltages and after all capacitors in the capacitor stack are charged, all capacitors of the capacitor stack are discharged into the first buffer capacitor outside the capacitor stack. Afterwards the capacitors of the capacitor stack are charged with negative voltages and after all capacitors in the capacitor stack are charged all capacitors of the capacitor stack are discharged into the second buffer capacitor outside the capacitor stack.

Since parasitic capacitances which arise at the interfaces to the surrounding have also to be charged at each charging procedure, it is most advantageous to always charge neighboring capacitor and not to "jump around" between the capacitors in the capacitor stack. Therefore, if bipolar charging of the capacitor stack is done the capacitors of the capacitor stack are sequentially charged, the n capacitors are discharged into a first buffer capacitor outside the capacitor stack, afterwards the n capacitors of the capacitor stack are sequentially charged in the reversed order and after the n capacitors are charged, the n capacitors are discharged into a second buffer capacitor outside the capacitor stack.

Accordingly, in a preferred embodiment of the invention after the n capacitors of the capacitor stack are sequentially charged the n capacitors are discharged into a first buffer capacitor outside the capacitor stack, afterwards the n capacitors of the capacitor stack are sequentially charged in the reversed order and after the n capacitors are charged the n capacitors are discharged into a second buffer capacitor outside the capacitor stack.

According to the invention the n capacitors of a capacitor stack can be discharged at once into one capacitor of a further capacitor stack.

The charging sequence for the second capacitor stack is derived from the first stack and couples to its timing. Instead of discharging the first capacitor stack into a buffer capacitance, it is discharged into one of the capacitors forming the second capacitor stack. Fundamentally it could be any of capacitors of the second capacitor stack, but practically the charging of the second capacitor stack should follow the same method already described. Which means charging of the capacitors of a capacitor stack should be done by charging neighboring capacitors. As the second capacitor stack is also loaded with some parasitic capacitance to the outside, sequentially charging the second stack as described will keep the charge flown into the parasitic capacitances to a minimum at each step.

One of the embodiments of the discharge circuit is a bipolar setting. This allows the charging of the second capacitor stack with negative and positive charge depending on the sequence. When the negative charge is transferred to the second capacitor stack, care has to be taken that the transistor switches are operated such that the charge on the stack is added with reverse polarity, so that this charge is accumulated on the second stack and not subtracted.

Parallelizing the sequential charge collection according to the invention, energy collection is multiplied and therefore the output-power of the device is increased.

In one embodiment of the invention the neural tissue stimulator comprises at least one further capacitor. The further capacitor can serve as buffer capacitor for the harvested energy or for energy which is transferred from an external energy source.

In one embodiment of the invention the neural tissue stimulator is adapted to perform several harvesting cycles during a singular cellular cycle in order to additionally optimize the harvested energy amount.

According to the invention energy harvesting can be done on one microneedle of the array of microneedles, on several microneedles of the array of microneedles or on all of the microneedles of the array of microneedles simultaneously.

Furthermore, in one embodiment of the invention a selection mechanism is implemented to select high yielding microneedles of the array of microneedles for energy harvesting and to discard low yielding microneedles of the array of microneedles. In one embodiment of the invention it is programmed which microneedles of the array of microneedles are utilized for energy harvesting. This is done via the external programmer unit. In a further embodiment of the invention the microneedles of the array of microneedles which are utilized for energy harvesting are selected due to the cellular electrical energy sensed by the individual microneedles of the array of microneedles. This is regulated internally by the sequence control circuit on the chip, advantageously no regulation by the external programmer unit is necessary. Thereby, the microneedles of the array of microneedles are selected for energy harvesting that achieve the highest energy yield.

According to the invention the neural tissue stimulator is adapted to be electrically self-sufficient due to harvesting of electrical energy from nerve cells. Since the harvested energy is uses to operate all functions of the neural tissue stimulator, the neural tissue stimulator of the present invention is not dependent on a power supply from a battery, which means the neural tissue stimulator according to the invention is electrically self-sufficient, which means electrically autonomous. All disadvantages associated with battery operation are eliminated. Hence, the device can be fully implanted into the intradural cavity and there is no need for any kind of recharge procedure for a battery or even a whole replacement of a neural tissue stimulator by a new one due to an empty battery.

According to the invention, sensing of the amplitude of the cellular electrical activity and energy harvesting happen together on a microneedle. If a cellular electrical activity above the reference level is detected, harvesting of electrical energy starts. In one embodiment of the invention, harvesting is carried out with repeated charging cycles until the cellular electrical activity falls below the reference level. Which means the microneedle harvests cellular electrical energy multiple times throughout a singular cellular cycle. In this embodiment the time interval for energy harvesting depends on the rate of nerve cell depolarization. In a further embodiment of the invention harvesting is carried out until a programmable time-out is reached. In this case the programmable time-out could be between 200 ms and 300 ms.

Pacing

According to the invention, every microneedle of the array of microneedles is adapted to be able to emit an electrical pulse. The electrical pulse is suited to electrically stimulate live tissue. According to the invention, every microneedle of the array of microneedles is able to emit a monophasic or a biphasic pulse in the tissue. The voltages of the electrical pulse typically range from 10 mV to 2 V and the pulse lengths varies from 0.2 ms to 2.0 ms. If it is a bipolar pulse the voltages of the electrical pulse typically range from 10 mV to 2 V and −10 mV and 2 V. According to the invention the electrical pulse is generated utilizing the harvested energy. Emitting of an electrical pulse is controlled by the sequence control circuit on the chip.

After an electrical pulse is applied, a cellular activity is initiated. Starting from the location in the brain, where the pulse is applied through the microneedle of the array of microneedles, the electrical activation propagates through the entire brain autonomously. No further pulse or action is required, once the pulse voltage exceeds the energy needed to activate the tissue.

As already described, in principal each microneedle of the array of microneedles is able to emit an electrical pulse. In a preferred embodiment of the invention one microneedle of the array of microneedles is selected to emit an electrical pulse if necessary. The respective microneedle of the array of microneedles is selected via the external programmer unit.

In one embodiment of the invention, the functionality to emit an electrical pulse is programmable for each microneedle of the array of microneedles. An algorithm-based comparison of stimulation thresholds selects the microneedle of the array of microneedles with the lowest stimulation threshold. Advantageously, by utilizing the microneedle of the array of microneedles having the lowest stimulation threshold minimizes the voltage of the electrical pulse emitted, which minimizes the energy consumption of the neural tissue stimulator.

While every microneedle is able to harvest cellular energy, to electrically stimulate live tissue and to sense intrinsic cellular electrical activity, the microneedles are not programmed to perform all three functionalities at the same time. Sensing of cellular electrical activity and harvesting of cellular energy is performed at one microneedle at the same time as already described. In one embodiment of the invention, sensing of cellular electrical energy and emitting an electrical pulse is done at the same microneedle of the array of microneedles. In a preferred embodiment of the invention at least one of the microneedles of the array of microneedles senses the cellular electrical activity and harvests cellular energy and at least one of the microneedles of the array of microneedles is used for emitting an electrical pulse if needed.

In one embodiment of the invention at least one microneedle of the array of microneedles used to emit an electrical pulse is set by programming during implantation of the neural tissue stimulator by the external programmer unit. In a further embodiment of the invention, at least one microneedle of the array of microneedles used to emit an electrical pulse is set by programming any time after the implantation by the external programmer unit.

In a preferred embodiment those microneedle or microneedles of the array of microneedles are selected to emit an electrical pulse if needed which has/have the lowest pace-threshold. Every microneedle of the array of microneedles has its own pace-threshold. The pace-threshold is defined as the energy needed to activate the tissue. Pace-thresholds are defined by the external programmer unit based on the sensed amplitude of the cellular electrical activity. This is performed automatically on the chip or by the external programmer unit.

In one embodiment the neural tissue stimulator is adapted to undertake an algorithm-based combination and/or comparison of sensed cellular electrical activity from multiple microneedles, which is done by the external programmer unit. This is useful to assess an automatic reference level and pace-threshold or for an automatized optimization of microneedle function adjudication.

Due to the brain activity during one action potential the amplitude of the cellular electrical activity reaches the reference level, rises and falls again below the reference level. In case of normal brain activity this process is repeated for every action potential. After a certain time after the sensed amplitude of the cellular electrical activity has exceeded the reference level and has been fallen again below the reference level it is expected that the sensed amplitude of cellular electrical activity exceeds again the reference level due to the next depolarization event. One of the cycles of cellular electrical activity caused by an action potential is called cellular cycle in the following description.

In one embodiment of the invention pacing is done in at any time point independently of the sensed cellular electrical activity.

According to a further embodiment of the invention, if the cellular electrical activity exceeds the reference level within an action potential, a time window starts. It is expected that inside a given cellular cycle time the sensed cellular electrical activity falls below the reference levels and rises again until it exceeds the reference level due to the start of the following cellular cycle. If no cellular electrical activity is sensed above the reference level on all microneedles of the array of microneedles, which is above the respective reference level of the microneedles of the array of microneedles, an electrical pulse is emitted into the tissue at the end of the cellular cycle time. According to the invention the cellular cycle time is between 0.1 ms and 0.1 s. The cellular cycle time can also be given as stimulation frequency, whereby the stimulation frequency is defined as stimulationfrequency=1/cycle time. The cellular cycle time is set via the external programmer unit after implantation of the neural tissue stimulator and can be adjusted any time via the external programmer unit.

The cellular cycle time starts over again every time the sensed amplitude of the cellular electrical activity reaches the reference level and rises further. Further, the cellular cycle time starts over again after emitting an electrical pulse into the brain tissue. With the cellular cycle time it is monitored if intrinsic events appear in the expected time windows.

Advantageously, in a preferred embodiment, a microneedle of the array of microneedles which is programmed to emit an electrical pulse if needed, can also sense cellular electrical activity and harvest energy in a cellular cycle, when there is cellular electrical activity.

The neural tissue stimulator, according to the invention, provides several advantages, a number of which have already been described. Further, the neural tissue stimulator of the present invention has no wires which connect the neural tissue stimulator with the brain to serve as sensors for the cellular electrical activity or which serve to emit an electrical pulse to the tissue if necessary. These functions are all provided by the microneedles of the array of microneedles. All disadvantages associated with wires are omitted (e.g., wires are ingrown by connective tissue, and wires permanently crossing the dura).

Each of the microneedles of the array of microneedles represents a separate electrical connection into neural tissue if the neural tissue stimulator is implanted in a patient, wherein each of the microneedles of the array of microneedles is individually programmable by the external programmer unit. Thereby, the neural tissue stimulator comprises more electrical connections into neural tissue than any other device available today. Accordingly, a redundancy of electrical connections is provided by the neural tissue stimulator according to the invention. In contrast, state of the art neural tissue stimulators have only limited electrical connections. If that fails due to electrode problems or degradation of the electrical electrode/tissue interface (e.g., through aging, fibrosis or dislocation), patients need an operation and a new wire.

The redundancy of the microneedles ensures continuous neural tissue stimulator functionality even in case of degeneration of a single microneedle/tissue interface. If one microneedle degrades over time for whatever reason its function can be taken over by another microneedle of the array of microneedles with a better functionality. Advantageously, the microneedles functionality of every microneedle of the array of microneedles can be exchanged or replaced though configuration reprogramming throughout the entire device lifetime.

Further, due to the improved programmability of sensing and pacing due to programming options the energy consumption of the neural tissue stimulator according to the invention is less compared to the energy consumption of neural tissue stimulator of the state of the art.

Further, due to the improved programmability of sensing and pacing due to programming options the targeting specificity of neural tissue stimulation to distinct anatomical sites and depths within the central nervous system according to the invention is improved to neural tissue stimulator of the state of the art.

The neural tissue stimulator according to the invention provides an improved interpretability of electrical signals in the brain due to instant comparison of hundreds of independent electrical recordings. Moreover, an improved automatized threshold testing due to comparability of signals between neighboring microneedles of the array of microneedles is provided, where one is stimulating and the other one recording. Further, more targeted selection of brain pacing sites, is provided due to the availability of multiple anatomically redundant different spatial pacing locations.

Method for Stimulating Neural Tissue

Further, the present invention provides a method for stimulating neural tissue utilizing a neural tissue stimulator according to the invention, characterized in that the microneedles of the array of microneedles are inserted into neural tissue;

optionally a cellular cycle time is set;

at least one reference level for the cellular electrical activity is set;

at least one microneedle of the array of microneedles is set to emit an electrical pulse;

at least one microneedle of the array of microneedles is set to sense the amplitude of the cellular electrical activity and to harvest energy;

the amplitude of the cellular electrical activity is sensed and energy is harvested at least by one microneedle; and an electrical pulse is applied to the neural tissue by at least one microneedle of the array of microneedles;

wherein the electrical pulse is generated utilizing the harvested energy.

All features described for the neural tissue stimulator apply also for the method of the present invention and vice versa.

According to the method of the invention the distal ends of the microneedles of the array of a multiple of microneedles are inserted into neural tissue. The penetration depth of the microneedles of the array of microneedles is between 0.5 mm and 5 mm. Advantageously, the neural tissue stimulator is fixated through bio-adhesives on capsule and interposer layer.

In one embodiment of the invention the neural tissue stimulator is deployed through a catheter, which is advanced into the target zone of neural tissue stimulation.

Optionally a cellular cycle time and a reference level for the cellular electrical activity are set by the external programmer unit. In one embodiment the cellular cycle time is between 0.1 ms and 0.1 s. The cellular cycle time can also be given as stimulation frequency, thereby the stimulation frequency is the inverse of the cellular cycle time. According to the invention, the stimulation frequency is between 10 Hz and 10000 Hz. Further, at least one microneedle of the array of microneedles is set to emit an electrical pulse and at least one microneedle of the array of microneedles is set to sense cellular electrical activity and to harvest energy. This is also done via the external programmer unit. These steps can be done immediately after the implantation of the neural tissue stimulator. Advantageously, adjustments of these parameters can be done any time via the external programmer unit.

According to the method, the amplitude of the cellular electrical energy is sensed and energy is harvested at least by one microneedle of the array of microneedles. The harvested energy is collected into the at least one buffer capacitor. In one embodiment of the invention the harvested energy is collected into multiple buffer capacitors, wherein the multiple buffer capacitors constitute a buffer capacitors-array.

Further, an electrical pulse is applied to the neural tissue by at least one microneedle of the array of microneedles. Preferably, the electrical pulse is applied to the neural tissue by the microneedle of the array of microneedles having the lowest energy demand. The microneedle of the array of microneedles with the lowest energy demand is determined by the amplitude of the cellular electrical energy sensed by the microneedles of the array of microneedles.

In a further embodiment of the invention several microneedles of the array of microneedles are set to emit an electrical pulse. In one embodiment between 1 and 40 microneedles of 100 microneedles, preferably between 1 and 30 microneedles of 100 microneedles, most preferably 1 microneedle of 100 microneedles is set to emit an electrical pulse.

In one embodiment more than one microneedle is set to sense and harvest cellular electrical energy. Accordingly, in one embodiment all microneedles which are not set to emit an electrical pulse are set to sense and harvest cellular electrical energy.

The electrical pulse which is applied to the neural tissue is a monophasic pulse or a biphasic pulse. Both are commonly used in neural tissue stimulators.

In a further embodiment of the invention an electrical pulse is applied to the neural tissue by at least one microneedle of the array of microneedles if no cellular electrical activity is sensed anymore during the cellular cycle time with an amplitude above the reference level after the sensed amplitude of the cellular electrical activity has been fallen below the reference level once. Accordingly in one embodiment of the invention a cellular cycle time is set and the cellular cycle time starts if the amplitude of the cellular electrical activity sensed by at least one microneedle of the array of microneedles reaches the reference level of the corresponding microneedle of the array of microneedles or after a pulse is emitted into the neural tissue by at least one microneedle of the array of microneedles and that an electrical pulse is applied to the neural tissue by at least one microneedle of the array of microneedles if no cellular electrical activity with an amplitude above the reference level is sensed anymore during the cellular cycle time after the amplitude of the sensed cellular electrical activity has been fallen below the reference level.

BRIEF DESCRIPTION OF THE FIGURES

The invention is further described by 7 figures and 2 example.

DETAILED DESCRIPTION

Figure 1:
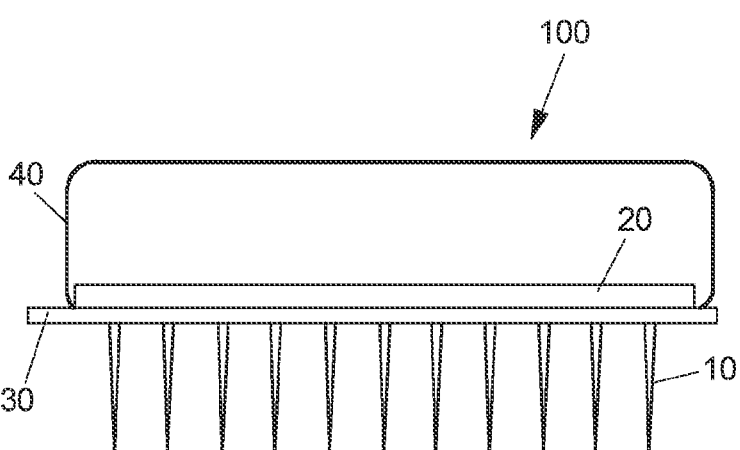
FIG. 1 illustrates one embodiment of the neural tissue stimulator according to the invention in side view.

FIG. 1 illustrates one embodiment of the neural tissue stimulator 100 according to the invention in side view. On top of the interposer layer 30 the chip 20 is positioned. Furthermore, a coil is positioned on top of the interposer layer 30, which is not shown in the figure for the sake of clarity. The chip 20 and the coil are covered by a lid 40. The lid 40 covers the chip 20 from the surrounding, wherein the lid 40 is sealed to the interposer layer 30. Sealing can be done by adhesives or soldering tin. If adhesives are used the adhesive should be hardened. However, the sealing should be bio-compatible and insensitive to body fluids. Accordingly, the lid 40 and the interposer layer 30 form a capsule for the chip 20. The lid 40 and the interposer-layer 30 shield the electronic parts from surrounding body-fluids like blood, e.g. from body fluids by forming a capsule. The proximal end of each microneedle 10 is soldered to the surface of the chip 20, which ensures that each microneedle 10 of the array of a multiple of microneedles has a direct contact to the chip 20. According to the invention each microneedle 10 of the array of a multiple of microneedles is isolated from each other microneedle 10 of the array of a multiple of microneedles. Further, the distal end of every microneedle 10 protrudes from the chip 20 and the interposer layer 30.

FIG. 2 (A) to (E) illustrate different embodiments of the neural tissue stimulator 100 according to the invention in top view. Again, the chip 20 and the coil are positioned on the interposer layer 30 and covered by the lid 40. The proximal end of each microneedle 10 is soldered by soldering points 11 to the surface of the chip 20, which ensures that each microneedle 10 of the array of a multiple of microneedles has a direct contact to the chip 20.

FIG. 2 (A) illustrates an I-shaped device according to the invention. The I-shaped device has a length a between 1 mm and 8 cm and a width b between 1 mm and 3 cm.

FIG. 2 (B) illustrates a T-shaped device according to the invention with a main body and one wing on each side of the main body. The length f of the main body is between 1 mm and 8 cm and the width c of the main body is between 1 mm and 3 cm. Both wings of the T-shaped neural tissue stimulator are positioned mirror-symmetrically to the main axis of the main body and have the same dimensions. The length d from the end of the first wing across the main body to the end of the second wing is between 1 mm and 3 cm. The width e of a wing on the widest point is between 1 mm and 3 cm.

In a further embodiment the neural tissue stimulator has an H-shape with a main body and two wings on each side of the main body (FIG. 2 (C)). The length f of the main body is between 1 mm and 8 cm. The width c of the main body is between 1 mm and 3 cm. All 4 wings of the H-shaped neural tissue stimulator are positioned mirror-symmetrically to the main axis of the main body, with 2 wings on each side of the main body. All wings and have the same dimensions. The wing-pair length d from the end of the first wing across the main body to the end of the second wing is between 1 mm and 3 cm. The width e of a wing on the widest point is between 1 mm and 3 cm. The longitudinal distance g between the 2 wing-pairs is between 1 mm and 7 cm.

The edges of the T-shaped or the H-shaped neural tissue stimulator can be rounded.

Figure 2A:
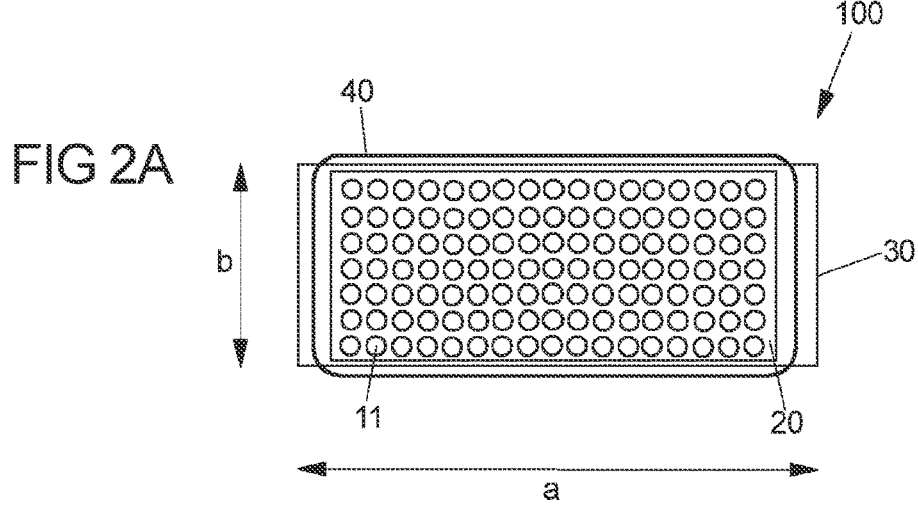
FIG. 2 (A) to (E) illustrates embodiments of the neural tissue stimulator according to the invention in top view.
Figure 2B:
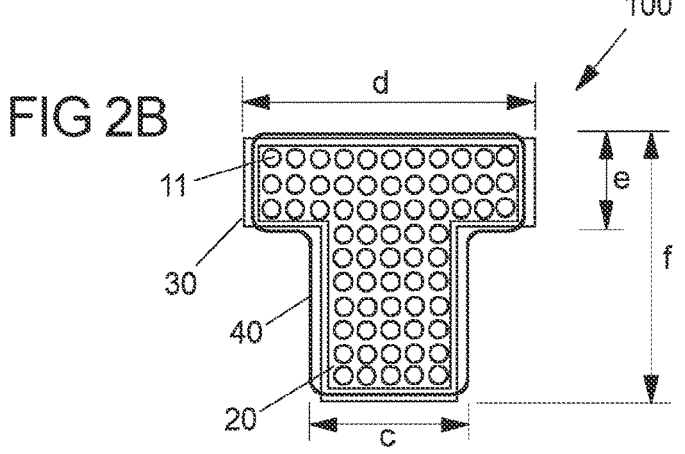
Figure 2C:
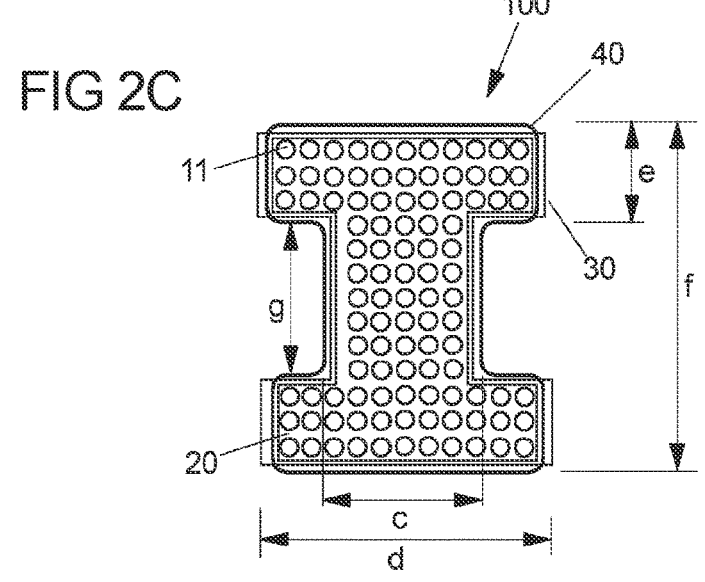
Figure 2D:
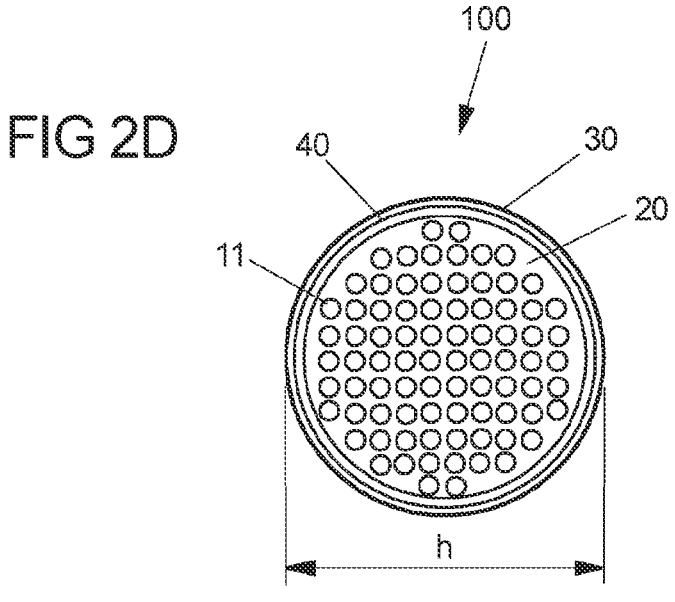
Figure 2E:
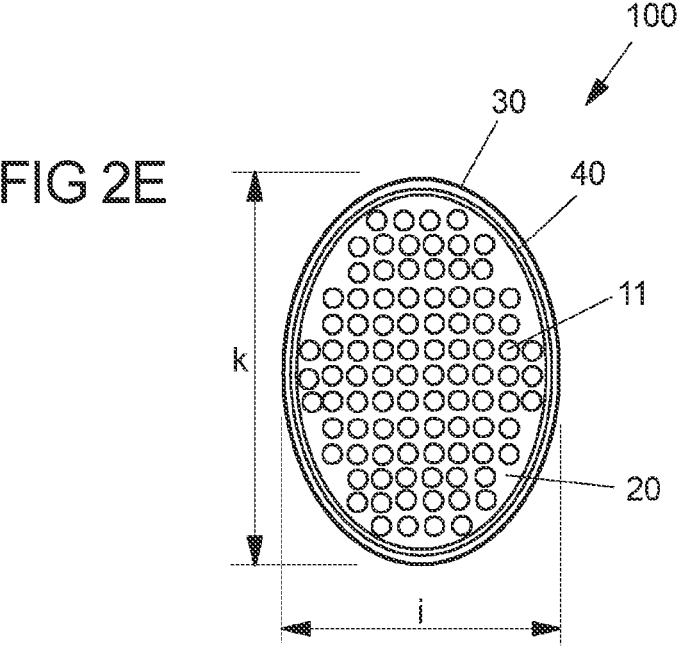

In a further embodiment the neural tissue stimulator has a circular (FIG. 2 (D)) or an O-shape (FIG. 2(E)). The circular shape has a diameter h between 1 mm and 8 cm. The oval O-shape has a length k between 1 mm and 8 cm and a width i between 1 mm and 3 cm.

Figure 3A:
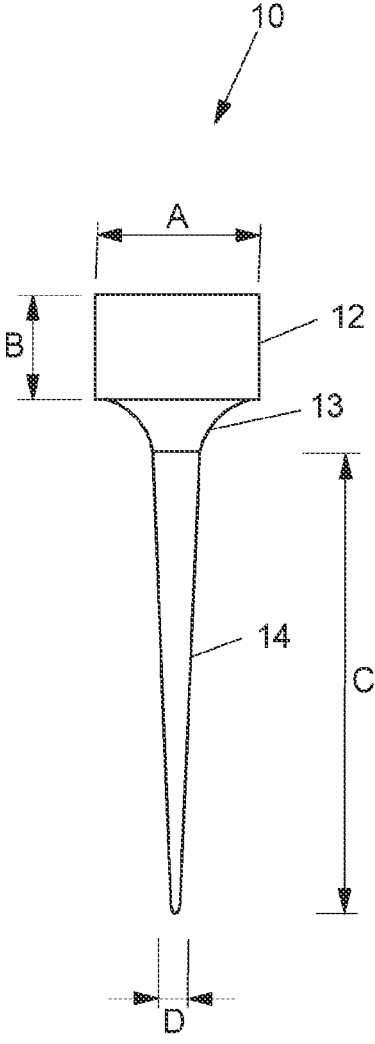
FIGS. 3 (A) and (B) illustrate embodiments of a microneedle of the array of microneedles.
Figure 3B:
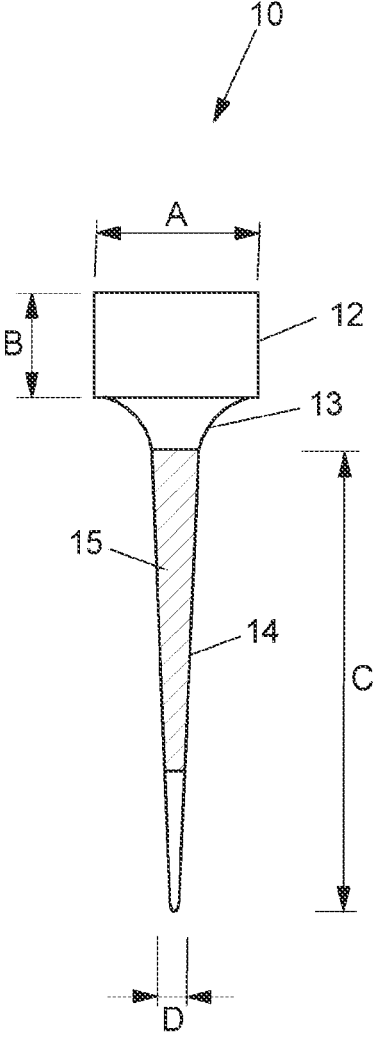

FIGS. 3 (A) and (B) illustrate embodiments of a microneedle 10 of the array of microneedles. The microneedle 10 comprises a proximal end 12, a tapered portion 13 and a distal end 14, wherein the tapered portion 13 connects the proximal end 12 with the distal end 14. Accordingly the tapered portion 13 is as short as possible and serves only as connection between the proximal end 12 and the distal end 14. In one embodiment of the invention, the microneedle 10 according to the invention has a proximal end 12, which is shaped cylindrical with a diameter A between 0.05 mm and 0.5 mm, preferably the proximal end has a diameter A of 0.2 mm and a height B between 0.05 mm and 0.5 mm, preferably with a height B of 0.2 mm. The distal end 14 is needle shaped and has a length C between 0.5 mm and 5 mm. The distal end 14 of the microneedle 10 is electrically conductive and shear stress resistant in the range of 5 to 50 Newton, which is comparable to the shear stress resistance of bonding wires. Preferably the microneedle is milled from one piece. Preferably, the diameter D of the distal end 14 of the microneedle is between 0.001 mm and 0.1 mm, preferably between 0.01 mm and 0.1 mm, most preferably the diameters D of the distal end 14 of the microneedle is 0.02 mm. Thereby, the distal end 14 of the microneedle 10 approximates cellular dimensions. While the distal end 14 of the microneedle illustrated in FIG. 3 (A) is electrical conductive over the whole length, the distal end 14 of the microneedle illustrated in FIG. 3 (B) is partially covered by an electrically insulating material 15. Therefore, only the uncovered part of the distal end 14 of the microneedle illustrated in FIG. 3 (B) is electrical conductive.

Figure 4:
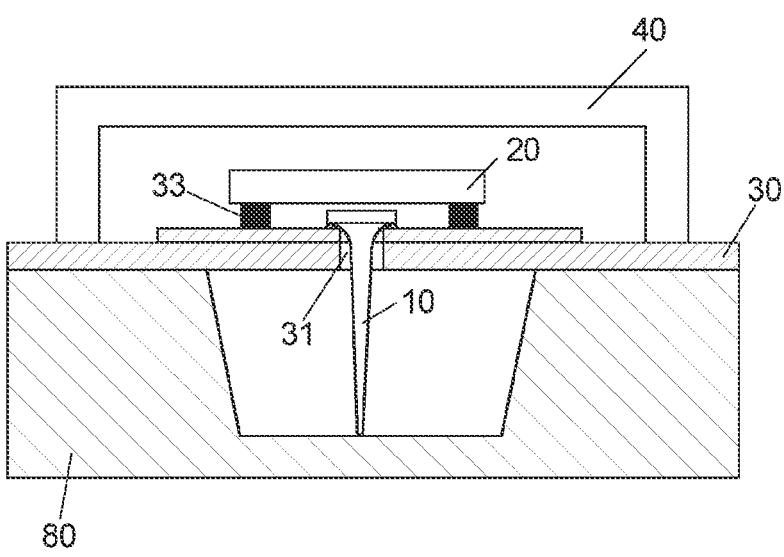
FIG. 4 illustrates an embodiment of the neural tissue stimulator.

FIG. 4 illustrates one embodiment of the neural tissue stimulator 100. An interposer layer 30 is provided which is adapted to connect the microneedles 10 of the array of microneedles with the chip 20. Further, the interposer layer 30 comprises holes 31 which are suited for receiving a microneedle 10. The interposer layer is covered by a temporary protective cover 80, which forms a sacrificial layer which is removed after assembly. A microneedle 10 is put inside the hole 31. The chip 20 is soldered to the interposer layer 30 by soldering points 33. The lid 40 is mounted to seal the device.

Figure 5:
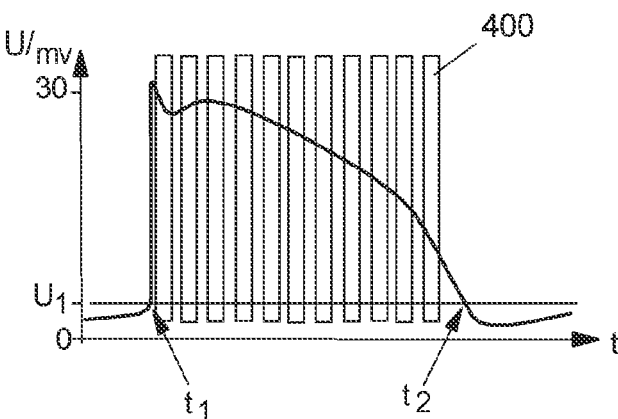
FIG. 5 illustrates harvesting during a cellular cycle.

FIG. 5 illustrates the timing of the harvesting during a cellular cycle. The graph illustrates the amplitude of the cellular electrical activity over time during one cellular cycle as sensed over a singular microneedle 10 of the array of microneedles. As the amplitude of the cellular electrical activity reaches the reference level $U_1$ of the corresponding microneedle the cellular cycle time $t_1$ starts and harvesting cycles 400 are started. Energy harvesting is done until the amplitude of the cellular electrical activity falls below the reference level $U_1$ again, which is at time point $t_2$.

Figure 6:
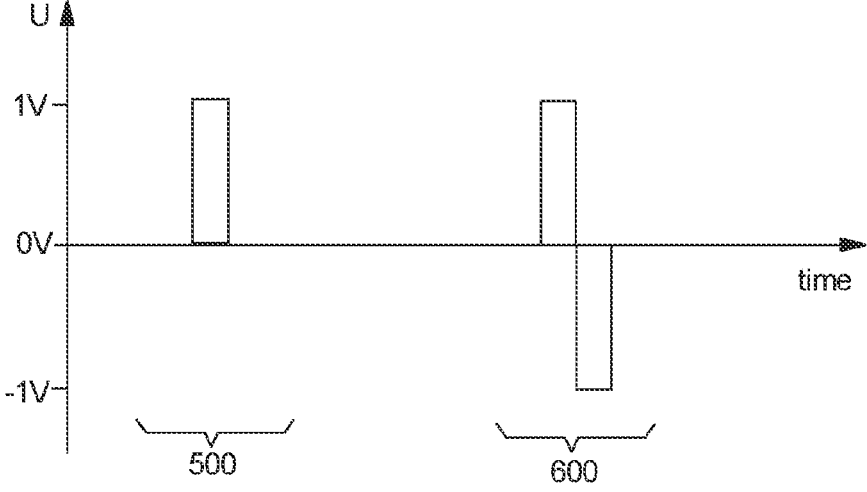
FIG. 6 illustrates different electrical pulses.

FIG. 6 illustrates different electrical pulses. According to the invention monophasic pulses 500 as well as bipolar pulses 600 can be emitted by the microneedles 10.

Figure 7:
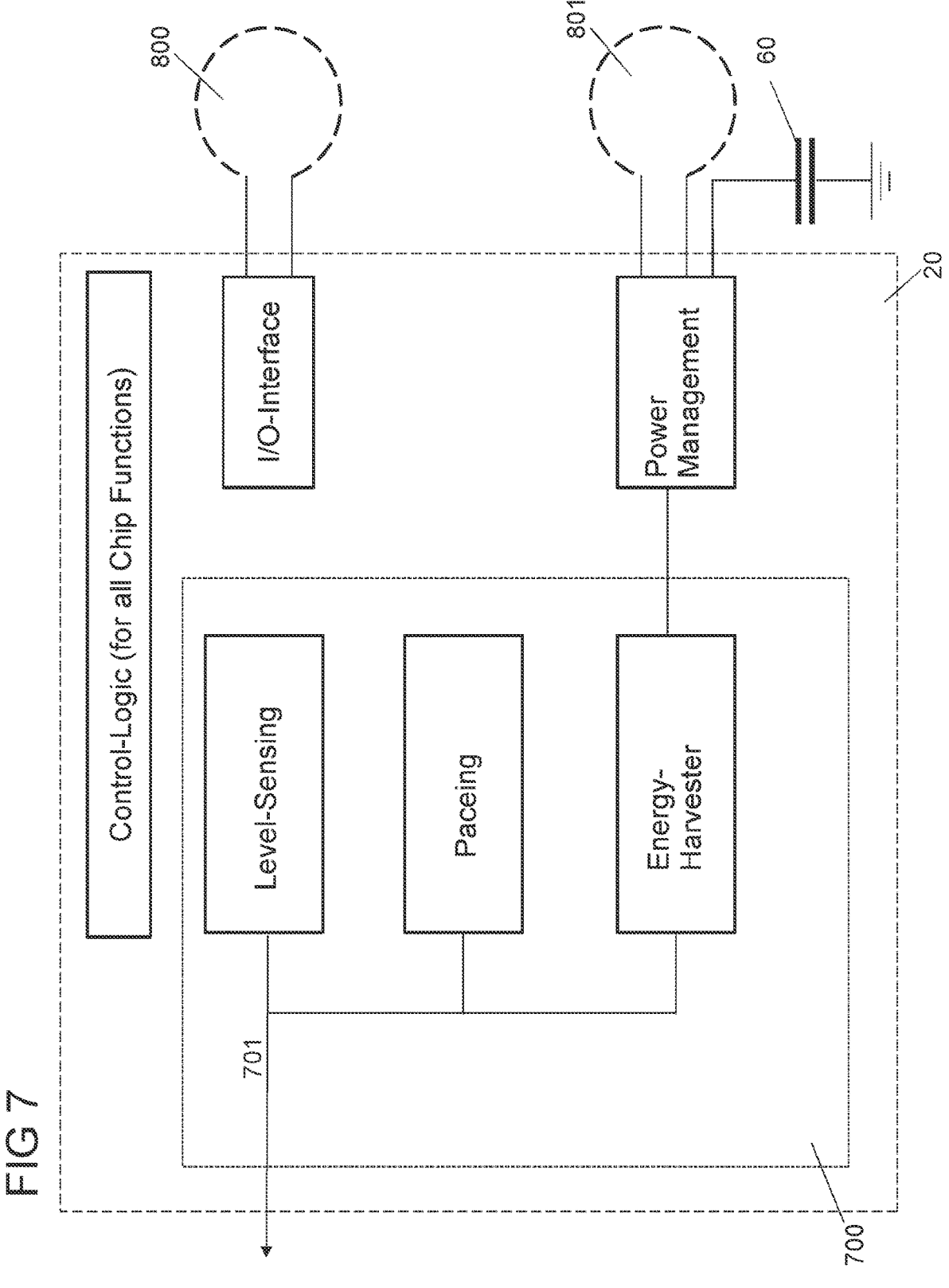
FIG. 7 illustrates the functions of the neural tissue stimulator.

FIG. 7 illustrates the functions of the neural tissue stimulator 100. Chip 20, external capacitor 60, coil 800 working as an antenna, coil 801 used for power transmission are illustrated. Although the microneedles 10 are not illustrated in the scheme, box 700 illustrates the basic functions of the microneedles 10. Box 700 with the connection 701 to a microneedle, level sensing-function, pacing-function and energy harvesting function is repeated for every microneedle of the device, which means, typically over 100 times. For each microneedle 10 the three basic function (sensing, pacing and harvesting) are associated. Control-logic and programming, which are the sequence control circuit, determine which function is activated per microneedle 10, bringing a great deal of redundancy to the system.

Control-logic and several further functions are implemented within the chip 20. The power management interface receives power from the harvesters and also from an associated coil 801 which can be fed from an electromagnetic field, which is applied from the external programmer unit for startup. Later operation is assumed from the collected energy harvested from the heart beats and does not require electromagnetic feeding any more. Further, the power management interface connects to the further capacitor of the device, thereby receiving power from energy stored in the further capacitor 60.

The I/O-interface also uses a coil 800 for data transmission to the external programmer unit. It is conceivable that one coil 800, 801 alone can assume both functions: energy transport and data transport.

Example 1

A neural tissue stimulator 100 according to the invention was built with a T-shaped form, comprising a main body with a length f of 20 mm and a width c of 6 mm, wherein the main body comprised an array of 14×46 microneedles 10, which were soldered to a chip 20. The neural tissue stimulator 100 comprised two wings each with a width e of 6 mm. The length d was 18 mm. Each wing comprised an array of 14×14 microneedles 10, which were soldered to the chip, too. The chip 20 with the array of microneedles was soldered to an interposer layer 30. The chip 20 was covered by a lid 40. All in all the neural tissue stimulator comprised 1036 microneedles 10.

Example 2

An array of microneedles 10 was used in a device according to the invention, wherein each microneedle 10 had the following shape. Each microneedle 10 comprises a proximal end 12, a tapered portion 13 and a distal end 14, wherein the tapered portion 13 connects the proximal end 12 with the distal end 14. Accordingly, the tapered portion 13 is as short as possible and serves only as connection between the proximal end 12 and the distal end 14. The proximal end 12 was shaped cylindrical with a diameter A of 0.2 mm and a height B of 0.2 mm. The distal end 14 was needle shaped and had a length C of 5 mm. The diameter D of the distal end 14 of the microneedle was 0.02 mm. Thereby, the distal end 14 of the microneedle 10 approximates cellular dimensions. The distal end 14 of a part of the microneedles is covered with an electrically insulating material 15 from the tapered portion 13 up to a length of 2 mm. The distal end 14 of a further part of the microneedles is covered with an electrically insulating material 15 from the tapered portion 13 up to a length of 3 mm. And the distal end 14 of a third part of the microneedles is not covered with an electrically insulating material 15 at all. Thereby stimulation of neural tissue in certain layers is enabled.

REFERENCE LIST 10 microneedle
11 soldering point
12 proximal end
13 tapered portion
14 distal end
15 electrically insulating material
20 chip
21 wire
30 interposer layer
33 soldering point
40 lid
60 capacitor
80 protective cover
100 neural tissue stimulator
400 harvesting cycle
500 monophasic pulse
600 bipolar pulse
700 basic functions
701 connection to microneedle
800 coil
801 coil

The invention claimed is:

1. A neural tissue stimulator, comprising
a multiple of microneedles forming an array of microneedles;
a chip comprising at least one comparator with adaptive level, a sequence control circuit, at least one capacitor stack built by n capacitors and 2n switches, at least one buffer capacitor outside the at least one capacitor stack, at least two additional switches outside the at least one capacitor stack and a CMOS-Logic, wherein n∈N; wherein the n capacitors are adapted to be sequentially charged by at least one microneedle of the array of microneedles, which functions as DC input source, one after the other and wherein the 2n switches of the capacitor stack couple the n capacitors selectively to at least one microneedle of the array of microneedles and wherein the buffer capacitor outside the at least one capacitor stack is dedicated to be charged from the n capacitors of the capacitor stack at once;
an interposer layer comprising holes for the multiple of microneedles;
a lid;
at least one startup circuit device;
wherein the chip, is located on one surface of the interposer layer;

wherein the lid and the interposer layer form a capsule for the chip;
wherein each microneedle has a distal end which protrudes from the chip;
wherein
the neural tissue stimulator is adapted to be electrically self-sufficient due to harvesting of electrical energy from neural cells; and
the distal ends of at least two microneedles of the array of microneedles have a different electrical insolation.
2. A neural tissue stimulator according to claim 1, wherein the neural tissue stimulator further comprises at least one further capacitor.
3. A neural tissue stimulator according to claim 1, wherein the neural tissue stimulator comprises between 5 and 1 000 000 microneedles.
4. A neural tissue stimulator according to claim 1, wherein the distal end of at least one microneedle of the array of microneedles is at least partially covered by an electrically insulating material.
5. A neural tissue stimulator according to claim 1, wherein the neural tissue stimulator has an I-shape, T-shape, H-shape, circular or O-shape.
6. A neural tissue stimulator according to claim 1, wherein the neural tissue stimulator further comprises an external programmer unit.
7. A neural tissue stimulator according to claim 1, wherein every microneedle is adapted to be operable independent of the other microneedles.
8. A neural tissue stimulator according to claim 1, wherein the diameters of the distal ends of the multiple of microneedles are between 0.001 mm and 0.1 mm.
9. A neural tissue stimulator according to claim 1, wherein the microneedles comprise a material of the group comprising Platin/Iridium (PtIr), gold, and fine metals.
10. A neural tissue stimulator according to claim 1, wherein each microneedle is adapted to be able to harvest cellular energy, to electrically stimulate live tissue and to sense intrinsic cellular electrical activity.
11. Method for stimulating neural tissue utilizing a neural tissue stimulator according to claim 1, wherein
the microneedles of the array of microneedles are inserted into neural tissue;
at least one reference level for cellular electrical activity is set;
at least one microneedle of the array of microneedles is set to emit an electrical pulse;
at least one microneedle of the array of microneedles is set to sense the amplitude of the cellular electrical activity and to harvest energy;
the amplitude of the cellular electrical activity is sensed and energy is harvested at least by one microneedle; and
an electrical pulse is applied to the neural tissue by at least one microneedle of the array of microneedles;
wherein the electrical pulse is generated utilizing the harvested energy.
12. Method according to claim 11, wherein a cellular cycle time is set and the cellular cycle time starts if the amplitude of the cellular electrical activity sensed by at least one microneedle of the array of microneedles reaches the reference level of the corresponding microneedle of the array of microneedles or after a pulse is emitted into the neural tissue by at least one microneedle of the array of microneedles and that an electrical pulse is applied to the neural tissue by at least one microneedle of the array of microneedles if no cellular electrical activity with an amplitude above the reference level is sensed anymore during the cellular cycle time after the amplitude of the sensed cellular electrical activity has been fallen below the reference level.

13. Method according to claim 11, wherein an electrical pulse is applied to the neural tissue by the microneedle having the lowest energy demand.

14. Method according to claim 11, wherein the electrical pulse is a monophasic pulse or a bipolar pulse.

15. Method according to claim 11, wherein the harvested energy is collected into the at least one buffer capacitor or a buffer capacitor-array.

* * * * *